(12) United States Patent
Novak

(10) Patent No.: US 8,943,613 B2
(45) Date of Patent: Feb. 3, 2015

(54) MORTUARY UNDERGARMENT WITH DRAINAGE SYSTEM

(76) Inventor: Ronald J. Novak, Royal Oak, MI (US)

( * ) Notice: Subject to any disclaimer, the term of this patent is extended or adjusted under 35 U.S.C. 154(b) by 893 days.

(21) Appl. No.: 12/632,907

(22) Filed: Dec. 8, 2009

(65) Prior Publication Data

US 2010/0138972 A1    Jun. 10, 2010

Related U.S. Application Data

(60) Provisional application No. 61/120,922, filed on Dec. 9, 2008.

(51) Int. Cl.
  *A41D 1/00* (2006.01)
  *A61F 5/449* (2006.01)
  *A61G 17/06* (2006.01)

(52) U.S. Cl.
  CPC .............. *A61F 5/449* (2013.01); *A61G 17/06* (2013.01)
  USPC .............................................................. 2/64

(58) Field of Classification Search
  USPC .......... 2/64, 456, 69.5, 82; 446/153, 202, 220
  See application file for complete search history.

(56) References Cited

U.S. PATENT DOCUMENTS

| | | | | |
|---|---|---|---|---|
| 1,170,293 | A * | 2/1916 | Loomis | 2/64 |
| 3,458,910 | A * | 8/1969 | Ritchey | 27/21.1 |
| 4,722,332 | A * | 2/1988 | Saggers | 602/62 |
| 5,435,009 | A * | 7/1995 | Schild et al. | 2/22 |
| 5,620,407 | A * | 4/1997 | Chang | 600/21 |
| 6,317,893 | B1 * | 11/2001 | Walton | 2/227 |
| 7,228,603 | B2 * | 6/2007 | Craig | 27/28 |
| 7,484,275 | B2 * | 2/2009 | Carroll et al. | 27/28 |
| 8,146,217 | B2 * | 4/2012 | Jensen et al. | 27/28 |
| 2006/0189905 | A1 * | 8/2006 | Eischen | 601/152 |
| 2011/0167601 | A1 * | 7/2011 | Jaskulske et al. | 27/22.1 |

* cited by examiner

*Primary Examiner* — Tejash Patel

(74) *Attorney, Agent, or Firm* — Vincent Re PLLC

(57) ABSTRACT

A liquid impermeable mortuary undergarment having resealable drainage ports mounted in the lower end of the undergarment's upper surface. The ports are positioned to grant ready access to drain any liquid accumulated in the undergarment.

5 Claims, 3 Drawing Sheets

MORTUARY UNDERGARMENT WITH DRAINAGE SYSTEM

CROSS-REFERENCE TO RELATED APPLICATIONS

This application claims priority of U.S. Provisional Patent Application filed Dec. 9, 2009 having Ser. No. 61/120,922.

FIELD OF THE INVENTION

The present invention relates to undertaking and, more particularly, to plastic undergarments for containing fluids escaping from a dead body.

BACKGROUND OF THE INVENTION

Typically, when a human corpse is prepared for a viewing or funeral, the body is preserved by embalming. In many situations, however, the embalmed body is susceptible to leakage of the embalming fluid along with additional fluids from the body. This is particularly the case when postmortem edema has occurred and/or when the body's skin has been compromised. Currently, this potentially bio-hazardous fluid is contained by dressing the body, or portions thereof, in impermeable plastic undergarments. In this way, any fluid that leaks from the body does not saturate the deceased's clothing or casket.

One disadvantage of current plastic undergarments is that frequently the volume of liquid escaping the body is too large to be contained by the undergarment resulting in overflowing.

There is therefore a need for a system and method for containing the fluids escaping from a dead body, while providing for a readily accessible and reusable means for draining the accumulating fluid as is deemed necessary.

SUMMARY OF THE INVENTION

Funeral directors typically maintain the deceased in their care with the deceased's head and upper body in a slightly elevated position to ensure that fluids in and out of the body flow toward the lower extremities (i.e., away from the head and face).

The present invention provides a novel covering for a dead body and method providing a reusable access port in the lower extremities of a fluid-impermeable garment. The access port is preferably located proximate to the lower-most portion of the garment and mounted to the front of the garment for ready access.

The port includes a plug or cap, which can be removed to grant access to the inner cavity of the garment for a drain tube to be inserted into the garment and into the pool of liquid to be drained. After the garment is drained, the plug is reinstalled upon the port resealing the garment.

It is an advantage of the present invention to provide a liquid impermeable undergarment having a front wall and rear wall which cooperate to define an internal cavity that contains at least a portion of a dead body. The undergarment including a re-sealable access means in the front wall proximate to its lower end which provides a passage through the undergarment into the internal cavity. The access means is sized to receive an elongated drain tube, which is insertable through the access means and into any fluid collected in the internal cavity.

It is another advantage of the present invention to provide a method for draining liquid from an internal cavity of an impermeable garment covering at least a portion of a dead body. The method includes the steps of: providing an access port having a removable cap; mounting the access port to a front wall of the garment proximate to a lower end of the garment, wherein the access port includes a passage through the front wall and into the internal cavity; unsealing the access port by removing the cap to open the passage; inserting an elongated tube through the access port passage into any liquid contained within the internal cavity; draining the liquid and removing the tube; and resealing the access port with the cap.

These and other objects, features and advantages of the present invention will become apparent from the following description when viewed in accordance with the accompanying drawings.

BRIEF DESCRIPTION OF THE DRAWINGS

The description refers to the accompanying drawings in which like reference characters refer to like parts throughout the several views, and in which.

DETAILED DESCRIPTION OF THE INVENTION

Figure 1:
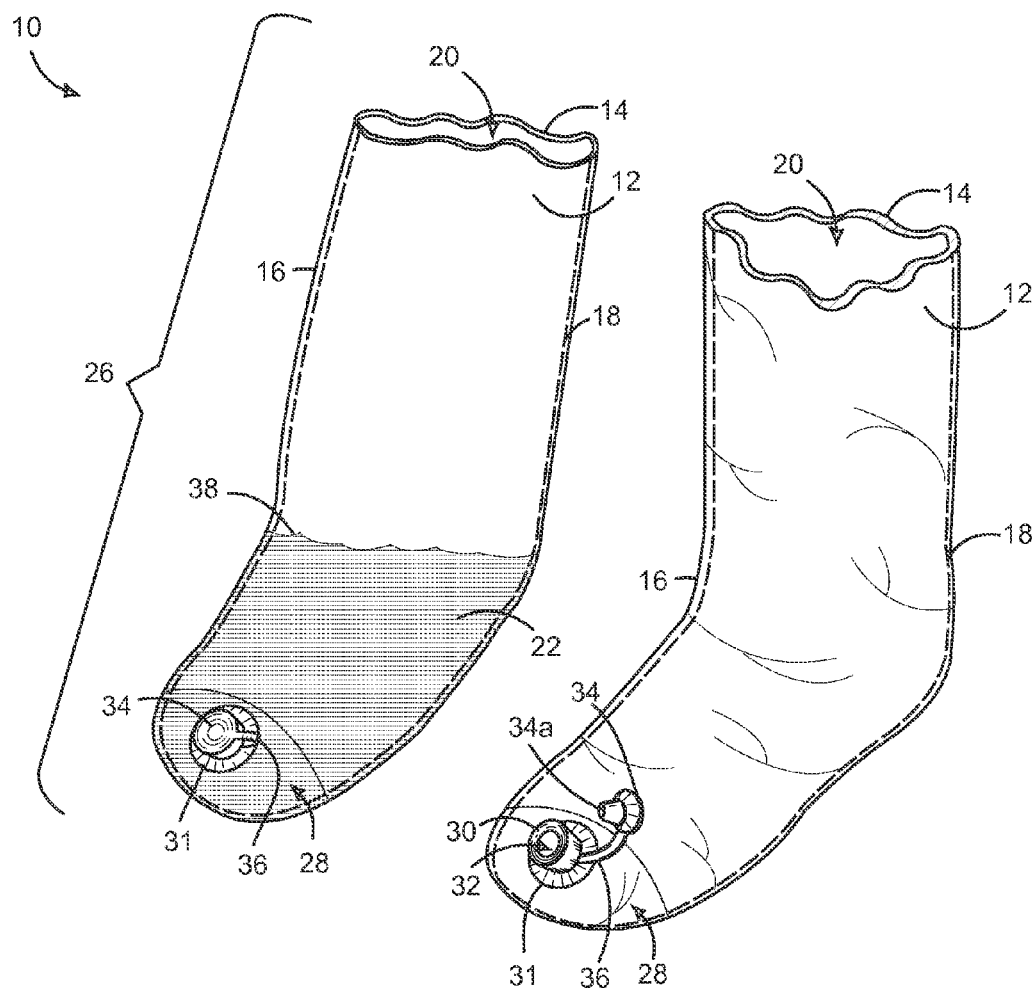
FIG. 1 is a partial perspective view of the lower portion of the present invention having one access port capped and the other un-capped.

Referring now to FIGs., the present invention is an undergarment 10 suitable for enclosing at least a portion of a dead body. Undergarment 10 includes a front wall 12 and rear wall 14 which are sealably interconnected along side seams 16, 18 through a conventional process, such as heat sealing. Front and rear walls 12, 14 are formed from a fluid-impermeable, durable, yet flexible plastic material, such as polyvinyl chloride. Walls 12, 14 are preferably two to eight mils (thousandths of an inch) thick.

Figure 2:
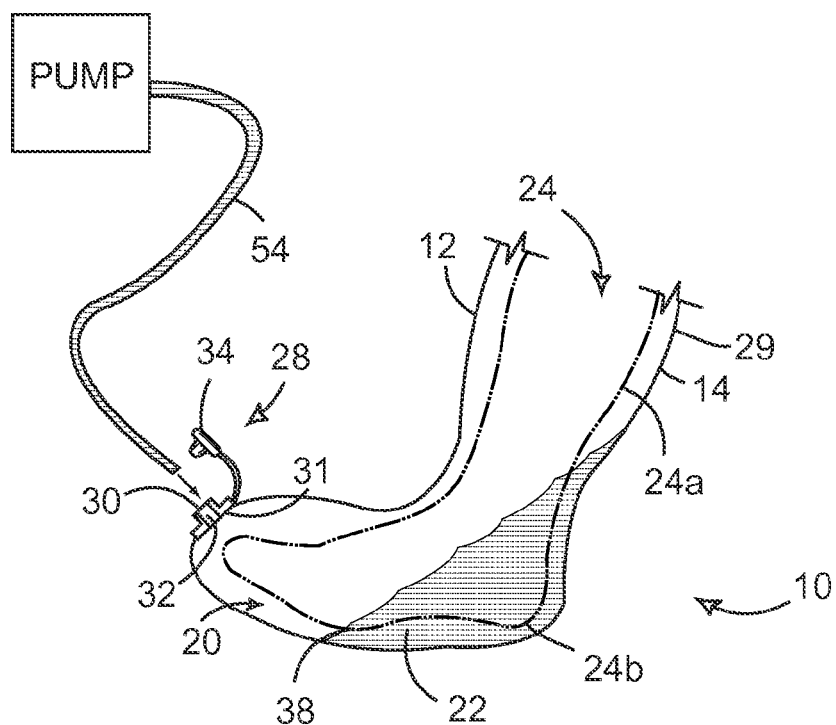
FIG. 2 is a partial side sectional view of the present invention in preparation for draining its internal cavity of liquids collected in the lower portion.
Figure 3:
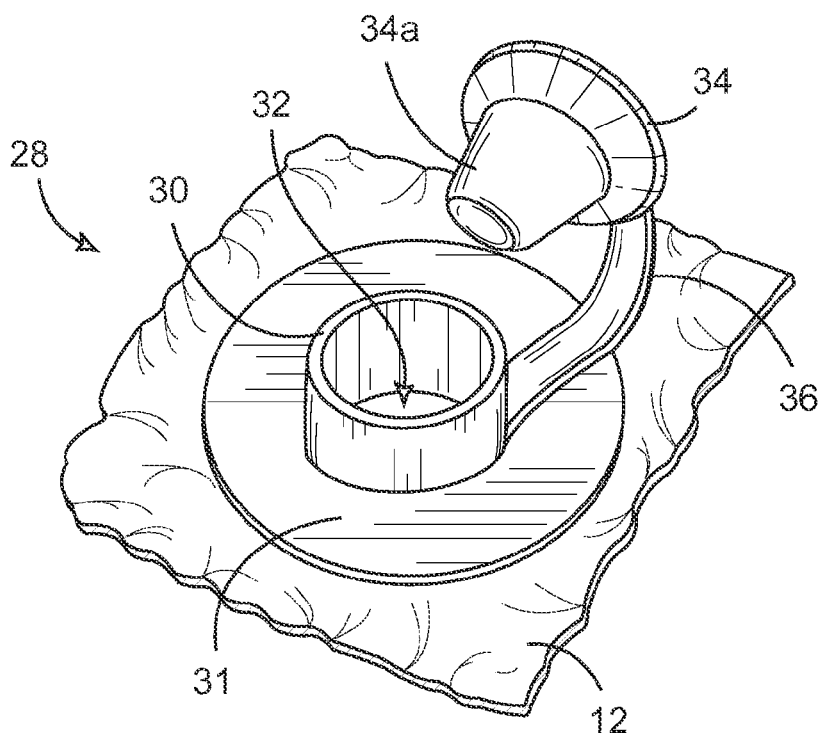
FIG. 3 is an enlarged view of one embodiment of the access port.

Walls 12, 14 cooperate to define an internal cavity 20, which retains any fluids 22 (or other material) escaping from the dead body 24 disposed therein. It should be appreciated that walls 12, 14 (and garment 10 in general) are configured such that cavity 20 is complementary in shape to the portion of the body contained within the garment 10. As shown in FIGS. 1 and 2, the lower portion 26 of the illustrated garment 10 is shaped to receive the lower leg 24a and foot 24b of a deceased person.

The lower portion 26 of garment 10 includes at least one access port 28 in front wall 12. As shown in the FIGs., two access ports are provide, one for each leg 29 forming the lower portion 26. Each access port 28 includes a tubular wall 30 that projects perpendicularly from an annular substantially flat mounting flap 31. Flap 31 extends radially from the bottom edges of wall 30 and provides a surface which can be affixed or bonded to front wall. In the preferred embodiment flap 31 abuts and is heat sealed to the outer surface of wall 12, producing a substantially air-tight bond. Wall 30 surrounds a passage 32 which passes through wall 12 and is in fluid communication with cavity 20.

Each port 28 includes a cover or plug 34, which is selectively removable from a closed position, where cover 34 seals the port 28 to an open position, where cover 34 is removed, granting access to cavity 20 through passage 32. In the embodiments illustrated, port 28 and cover 34 are a resilient frictional closure, having a male stopper or bung 34a which is frictionally received within the female passage 32 defined by wall 30. To avoid misplacement, port 28 preferably includes a tether 36 which is affixed to the cover 34. It should be appreciated that the frictional closure of access port 28 is exemplary in nature and substantially any other type of re-sealable closure may be used in its place, such as complementary threaded portions of the wall 30 and cover 34.

As best shown in FIG. 2, access port 28 is mounted to the front wall 12 to allow ready access to the port when the body 24 is lying prone (typically with its head and upper body slightly elevated relative to the lower body). Port 28 is further located in the lower portion 26 above the "waterline" 38 of accumulated escaping fluids 22 contained by the sealed undergarment 10 when the body 24 is in a slightly head/upper body elevated position. In the embodiments illustrated, port 28 is located in the dorsum (i.e., top of the foot) portion 40 of the undergarments above the feet 24b. By locating the port 28 in the dorsum portion 40 of front wall 12 along with its location above the waterline 38, a funeral director can readily access the port 28 without undressing the body. Mounting the port 28 above a typical waterline 38 further prevents the liquid 22 trapped in the undergarment 10 from immediately escaping or purging once cap 34 is removed. In other non-limiting embodiments, ports 28 may be located in other advantageous positions, such as the toe portion of the undergarment, which grant ready access to the accumulated fluid, while remaining above a typical waterline 38.

Figure 4:
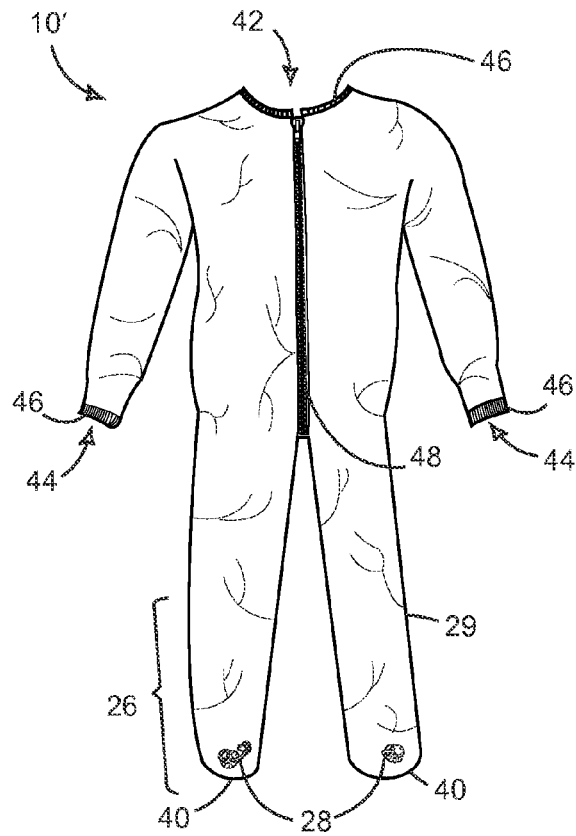
FIG. 4 is a plan view of a unionall embodiment of the present invention.
Figure 5:
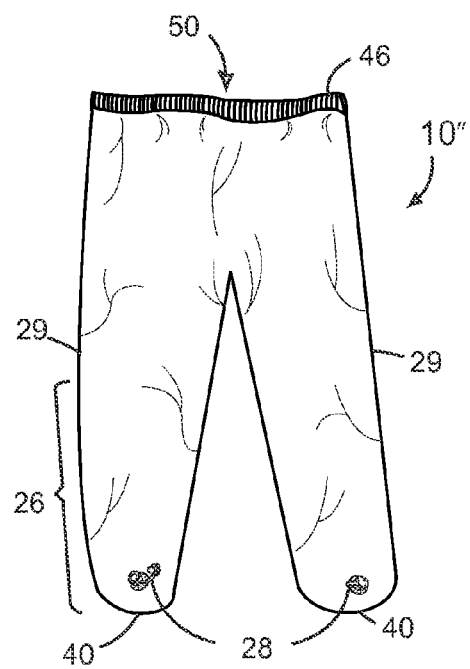
FIG. 5 is a plan view of a capri pant embodiment of the present invention.
Figure 6:
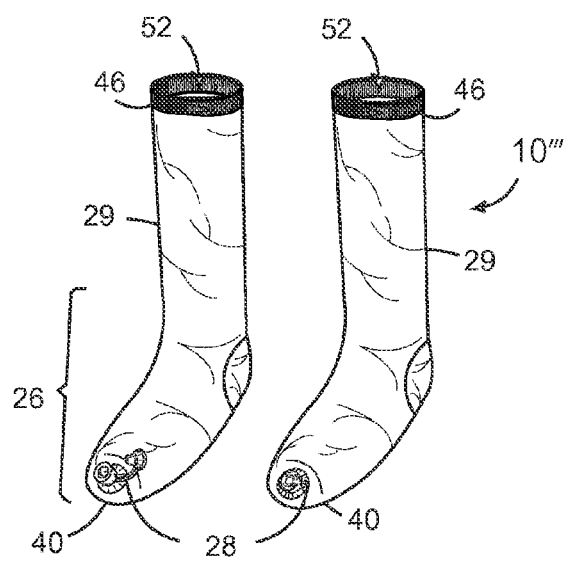
FIG. 6 is a plan view of an embodiment of the present invention as a pair of stockings.

As illustrated in FIGS. 4-6 the present invention can be configured in various types of mortuary undergarments. These embodiments can be described as gravity sensitive types of mortuary garments, which collect a relatively large amount of body-escaping fluids 22 in their lowermost portions 26. A unionall 10' (FIG. 4), which encloses substantially the entire body of the deceased, has fully enclosed legs 29 and feet/toe portion 40 and has a head opening 42 and hand openings 44, each surrounded by an elastic fringe 46 which seals the opening when body 24 is placed within the undergarment 10'. A zippered opening 48 runs down the chest of the unionall to insert the body into the cavity.

FIGS. 5 and 6 illustrate a pants 10" configuration and pair of stockings 10'" configuration, respectively. Pants 10" has fully enclosed legs 29 and feet/toe portion 40 and has a waist opening 50 surrounded by an elastic fringe 46 which seals the opening when body 24 is placed within the undergarment 10". Similarly, each stocking 10'" has enclosed legs 29 and feet/dorsum portion 40 and has a mid-thigh opening 52 surrounded by elastic fringe 46 which seals the opening when the legs of a body 24 are placed therein.

As described above, each of the embodiments 10, 10', 10", and 10'" include a pair of access ports 28 and their covers 34 are mounted to the lower portion 26 of the undergarments, which are proximate to, but elevationally above, the lower-most portion, e.g., the foot's heel.

In operation, a funeral director would place the body 24 (or portion thereof) within the cavity 20 of the present invention prior to dressing the deceased for the funeral/viewing. Any fluid 22 that may seep or otherwise escape from the portion enclosed by the undergarment 10 will collect in the elevationally lower-most portion, generally shown at 26. The funeral director can monitor the fluid volume or level in the undergarment 10 and, if necessary, drain the accumulated fluid 22 by opening an access port 28 by removing the cover 34, inserting a drain tube 54 and pumping the fluid from the cavity 20. Once the fluid is removed, the user can re-seal port 28 with cover 34 ensuring that no liquids will overwhelm the undergarment and overflow.

From the foregoing description, one skilled in the art will readily recognize that the present invention is directed to an improved system and method for containing and draining fluids that leak from a dead body. While the present invention has been described with particular reference to various preferred embodiments, one skilled in the art will recognize from the foregoing discussion and accompanying drawing that changes, modifications and variations can be made in the present invention without departing from the spirit and scope thereof. Particularly, that the above-described undergarment 10 can be substantially any style or type of garment configured to provide an impermeable barrier for human remains.

The invention claimed is:

1. An apparatus comprising a drainable mortuary undergarment for covering a lower portion of a dead body, the apparatus comprising:
    the mortuary undergarment configured to cover at least each of two leg portions of the lower portion of the dead body and leave uncovered for funeral proceedings an upper portion of the dead body, the undergarment comprising:
        a liquid impermeable body covering configured in a shape of the lower portion of the dead body, the shape including at least two separate and distinct leg covers providing a gap between the leg covers, and having an internal cavity that selectively receives the lower portion of the dead body, the internal cavity holding fluid emanating from the portion of the dead body;
        an access port to a front wall of the covering proximate to a lower end of one of the leg covers of the liquid impermeable body covering, wherein the port has a removable cap and includes a passage through the front wall and into the internal cavity, for the purpose of draining the fluid from the internal cavity; and
        a sealing fringe located around an opening of the liquid impermeable body covering configured to seal against the body and prevent the fluid from leaking past the sealing fringe.

2. The apparatus of claim 1, wherein said removable cap selectively seals said passage.

3. The apparatus of claim 1, wherein said access port includes an annular flap depending from a lower end of a tubular body and wherein said annular flap is sealed to an outer surface of said front wall.

4. The apparatus of claim 1, wherein the sealing fringe comprises an elastic fringe.

5. The apparatus of claim 1, wherein the liquid impermeable body covering is further configured in a shape of two arms of the dead body.

* * * * *